United States Patent [19]
Wachs et al.

[11] Patent Number: 6,037,290
[45] Date of Patent: Mar. 14, 2000

[54] IN SITU REGENERATION OF METAL-MOLYBDATE CATALYSTS FOR METHANOL OXIDATION TO FORMALDEHYDE

[75] Inventors: Israel E. Wachs, Bridgewater, N.J.; Laura E. Briand, LaPlata Buenos Aires, Argentina

[73] Assignee: Lehigh University, Bethlehem, Pa.

[21] Appl. No.: 09/287,019

[22] Filed: Apr. 6, 1999

Related U.S. Application Data

[60] Provisional application No. 60/081,764, Apr. 15, 1998.

[51] Int. Cl.$^7$ ........................................... B01J 20/34
[52] U.S. Cl. .............................. 502/34; 502/20
[58] Field of Search .......................... 502/20, 34

[56] References Cited

U.S. PATENT DOCUMENTS

| | | |
|---|---|---|
| 1,913,405 | 6/1933 | Meharg et al. |
| 3,236,782 | 2/1966 | Koch . |
| 3,882,159 | 5/1975 | Callahan et al. |

FOREIGN PATENT DOCUMENTS

| | | |
|---|---|---|
| 0 199 359 A2 | 10/1986 | European Pat. Off. |
| 0 732 146 A1 | 9/1996 | European Pat. Off. |
| 814076 | 5/1959 | United Kingdom . |
| 1191143 | 5/1970 | United Kingdom . |
| 1263139 | 2/1972 | United Kingdom . |
| 2 144 049 | 2/1985 | United Kingdom . |

OTHER PUBLICATIONS

Knozinger, H.; Taglauer, E. *Catalysis* 1993, 10, 1, No Month Available.
Machej, T.; Haber, J.; Turek A.M.; Wachs, I.E. *Appl. Catal.* 1991, 70, 115, No Month Available.
Honicke, D.; Xu, J. *J. Phys. Chem.* 1988, 92, 4699, No Month Available.
Hu, H.; Wachs, I.E. *J. Phys. Chem.* 1995, 99, 10911, No Month Available.
Stampfl, S.R.; Chen, C.; Dumesic, J.A.; Niu, C.; Hill, Jr., C.G. *J. Catal.* 1987, 105, 445, No Month Available.
Deo, G.; Wachs, I.E. *J. Phys. Chem.* 1991, 95, 5889, No Month Available.
Wang, C.B.; Xie, Y.C.; Tang, Y.Q. Science in China 1994, 37, 1458, No Month Available.
Margraf, R.; Leyrer, J.; Taglauer, E.; Knozinger, H. *Surface Sci.* 1987, 189/190, 842, No Month Available.
Leyrer, J.; Zaki, M.I.; Knozinger, H. *J. Phys. Chem.* 1986, 90, 4775, No Month Available.
Leyrer, J.; Mey, D.; Knozinger, H. *J. Catal.* 1990, 124, 349, No Month Available.
Cheng, W.H. *J. Catal.* 1996, 158, 477, No Month Available.
Holstein, W.; Machiels, C.J. *J. Catal.* 1996, 162, 118, No Month Available.
Segawa, K.; Hall, W.K. *J. Catal.* 1982, 77, 221, No Month Available.
Turek, A.M.; Wachs, I.E.; DeCanio, E. *J. Phys. Chem.* 1992, 96, 5000, No Month Available.
Farneth, W.E.; Staley, R.H.; Sleight, A.W. *J. Am. Chem. Soc.* 1986, 108, 2327, No Month Available.
Tatibouet, J.M. *Appl. Catal.* A 1997, 148, 213, No Month Available.
Delmon, B.; Froment, G.F. *Catal. Rev.–Sci. Eng.* 1996, 38, 69, No Month Available.
Banares, M.; Hu, H.; Wachs, I.E. *J. Catal.* 1994, 150, 407, No Month Available.

*Primary Examiner*—Elizabeth D. Wood
*Attorney, Agent, or Firm*—Banner & Witcoff, Ltd.

[57] ABSTRACT

The method of the present invention involves in situ regeneration of metal-molybdate catalyst for methanol oxidation to formaldehyde comprising the step of regenerating spent metal-molybdate catalyst with an oxygen-free gas stream comprising methanol and an inert gas for a sufficient time and at an elevated temperature to regenerate the metal-molybdate catalyst.

7 Claims, 7 Drawing Sheets

IN SITU REGENERATION OF METAL-MOLYBDATE CATALYSTS FOR METHANOL OXIDATION TO FORMALDEHYDE

This application claims the priority benefits from the U.S. provisional application Ser. No. 60/081,764 filed Apr. 15, 1998.

FIELD OF THE INVENTION

The present invention is directed to the in situ regeneration of metal-molybdate catalysts suitably used for methanol oxidation to formaldehyde.

BACKGROUND OF THE INVENTION

New or fully regenerated catalysts will have both $MoO_3$ and $Fe_2(MoO_4)_3$ phases uniformly throughout the catalyst. However, when these catalysts are employed industrially for the manufacture of formaldehyde via methanol oxidation, they preferentially lose the $MoO_3$ component. This component is mainly lost from the catalyst placed at the top (inlet) and any "hot" spot regions of the catalytic reactor, leaving this catalyst with surface regions having the less efficient $Fe_2(MoO_4)_3$ component. This decreases the efficiency, activity and selectivity of the catalyst, thereby requiring regeneration of the catalyst.

Regeneration methods prior to the present invention have had a number of significant disadvantages. Notably, regeneration by prior art methods required removal of the catalyst bed, regeneration in a separate vessel, and reloading of the catalyst bed. Such a sequence of steps was very expensive and slow.

The non-uniform compositions of the resulting spent catalysts also created difficulties in uniform regeneration. In addition to the molybdenum trioxide component losses noted above from the top and hot spot regions, the catalyst at the bottom of the reactor collects and becomes enriched in molybdenum trioxide component.

Thus, there is a need for new methods of regeneration of these catalysts. More specifically, there is a need for methods that redistribute the molybdenum trioxide component of the individual catalyst particles in order to increase the composition homogeneity while increasing average catalyst activity and formaldehyde selectivity.

The present invention fulfills this need by providing a new in situ method for redistributing the molybdenum trioxide component. Another objective of the present invention is to provide a method for obtaining more active catalysts, thereby resulting in reduced energy requirements because lower reactor temperatures will be needed to achieve complete methanol conversion. Yet another objective of the present invention is to increase the yield of formaldehyde from methanol oxidation, again resulting in reduced energy requirements of the process. These and other benefits of the present invention are described below.

BRIEF SUMMARY OF THE INVENTION

It has now been discovered that in situ regeneration of metal-molybdate catalysts can be achieved by treating spent metal-molybdate catalysts with a methanol/inert gas stream in the absence of oxygen. During this in situ regeneration method, $MoOCH_3$ complexes are formed, which draw out and redistribute the Mo component from the interior of the catalyst to the exterior of the catalyst, i.e., the active zone. It has been found that such treated catalysts are significantly more active and more selective in oxidation of methanol and the formation of formaldehyde therefrom than untreated spent catalyst.

The present invention provides the following additional benefits over prior regeneration methods. More specifically, the present method can be performed in-situ and does not require that the catalyst bed be unloaded. Additionally, the more active and selective catalysts made according to the present invention permit lower reactor temperatures to achieve complete methanol oxidation to formaldehyde. The yield of formaldehyde production is also increased which reduces the energy requirements and cost of the oxidation process. Waste products of carbon monoxide and dioxide are minimized while consumption of methanol is closer to ideal stoichiometry. These and other advantages will be readily recognized by those of skill in the art.

DETAILED DESCRIPTION OF THE PREFERRED EMBODIMENT

The present invention relates to a process for regenerating metal-molybdate catalysts used in the conversion of methanol to formaldehyde by contact in a flowing stream of oxygen-free gas containing methanol and an inert gas at conditions including a temperature of at least that typically used for the conversion of methanol to formaldehyde. Typical conditions useful for the regeneration process of the invention include an elevated temperature within the range from about 150°–500° C., preferably within the range of about 250°–350° C. for a period of at least about 30 minutes.

While not wishing to be bound by theory, it is believed that metal-molybdate catalysts at the top of the catalyst bed becomes "spent" when hot, flowing methanol removes molybdenum trioxide from the exposed catalyst surfaces by forming a volatile molybdenum trioxide at typical formaldehyde conversion temperatures. The regeneration process is intended to encourage the migration of molybdenum trioxide from inside the catalyst to the exposed outside catalytic sites by the same mechanism, namely, redistribution by volatilization in flowing methanol at temperatures on the order of those typically encountered as the catalyst became deactivated. In ring shaped catalyst solids, the molybdenum trioxide component is encouraged to move from the inner ring surface to the outer ring surface.

The regeneration process can be performed by passing an oxygen-free stream containing methanol in an inert gas (i.e., neither reducing nor oxidative toward the catalyst) through the catalyst bed in a direction opposite to the normal flow of reactants through the system, in the same direction of typical reactant flow, or radially inwardly or outwardly.

Catalysts that can be regenerated according to the present invention include supported or unsupported metal-molybdate complexes where the metal-molybdate complex is active for the conversion of alcohols to the corresponding aldehydes. Suitable sources of catalytically active metal include iron, lead, cadmium, bismuth, sodium, manganese, gadolinium, magnesium, copper, cobalt, tellurium, aluminum, chromium, and combinations thereof. Exemplary forms of catalytically active compositions that are formed by this process include $Fe_2(MoO_4)$, $PbMoO_4$, $CaMoO_4$, $Bi_2Mo_2O_9$, $Bi_3(FeO_4)(MoO_4)_3$ and other Bi—Mo—O family members, $Na_2MoO_4$, $Na_2Mo_2O_7$, $MnMoO_4$, $Gd_2(MoO_4)_3$, $MgMoO_4$, $CuMoO_4$, $CoMoO_4$, $Fe_2(MoO_4)_3$, $Te_2MoO_7$, $CoMoO_4$, $Al_2(MoO_4)_3$, and $Cr_2(MoO_4)_3$.

If supported, the preferred metal oxide supports include oxides of titanium, tin, aluminum, zirconium, cerium, niobium, tantalum, and mixtures thereof.

The catalysts of particular note for regeneration by the present process includes those containing iron—molybdate complexes. Such iron—molybdate catalysts for process have been made by coprecipitating ammonium molybdate (e.g., $(NH_4)Mo_7O_{24}\cdot 4H_2O$)) with iron nitrate solution at appropriate temperature and pH for precipitation. The precipitated solids are then washed, dried, and finished to make particulate catalysts for the oxidative conversion of methanol to formaldehyde. Alternatively, particles of each metal oxide are loaded into the reactor and allowed to form active catalyst in situ as described in my copending application, claiming the benefit of U.S. Provisional application 60/081, 950 entitled: "In Situ Formation of Metal Molybdate Catalysts," the utility application of which is filed concurrently herewith, and which application is herein incorporated by reference.

EXAMPLES

The following examples employed spent or used cylindrically shaped rings of iron—molybdate catalyst that had been made by Perstorp AB of Perstorp, Sweden and sold by Perstorp Polyols of Toledo, Ohio under the product designation KH-26L. The experiments were performed in a conventional plug flow reactor.

Example 1

By way of comparison, commercial KH-26L catalyst was compared to catalysts containing $MoO_3$, $Fe_2O_3$, NiO, coprecipitated $MoO_3/Fe_2(MoO_4)_3$, and mechanical mixtures of particles containing $MoO_3$, $Fe_2O_3$, NiO and $Fe_2(MoO_4)_3$. Table I sets forth methanol conversion to formaldehyde. As seen by the relative turnover frequencies (TOF, determined as the reaction rate divided by the number of surface active sites per surface area of catalyst), the most active catalysts are characterized by an excess of catalytic molybdenum trioxide. The number of surface active sites was determined by methanol chemisorption at 100° C.

TABLE 1

Methanol Oxidation Turnover Frequencies of
Pure Compounds and Mixtures Prepared by Different Synthesis Methods

|  | $S_{BET}$ ($m^2/g$) | Synthesis | Selectivity | TOF (308° C.) ($sec^{-1}$)[a] |
|---|---|---|---|---|
| $MoO_3$ | 5.0 | (Thermal Decomposition) | 88.0 | 5.3 |
| $Fe_2O_3$ | 21.4 | (Commercial) | 49.0 | 26.9 |
| NiO | 34.4 | (Thermal Decomposition) | — | 53.1 |
| $Fe2(MoO_4)_3$ (1.5)[b] | 9.6 | (Inorganic Coprecipitation) | 61.0 | 1.1 |
| $Fe2(MoO_4)_3$ (1.5) | 1.5 | (Organic Coprecipitation) | 58.0 | 1.8 |
| $Fe2(MoO_4)_3$ (1.1) | 3.9 | (Inorganic Coprecipitation) | 64.9 | 2.2 |
| $MoO_3/Fe_2(MoO_4)_3$ (2.2) | 3.0 | (Inorganic Coprecipitation) | 88.5 | 15.8 |
| $MoO_3$ + /$Fe_2(MoO_4)_3$ (2.2) | 3.5 | (Mechanical Mixture) | 88.3 | 14.8 |
| $MoO_3/Fe_2(MoO_4)_3$ (3.97) | 2.6 | (Mechanical Mixture) | 88.3 | 35.1 |
| $MoO_3$ + $Fe_2O_3$ (2.2) | 5.7 | (Mechanical Mixture) | 92.0 | 14.5 |
| $MoO_3$ + NiO (2.2) | — | (Mechanical Mixture) | — | 4.2 |
| Industrial Catalyst | 7.8 | (Coprecipitation) | 95.0 | 29.6 |

[a]The activity of the mixtures were obtained at 300° C. and extrapolated to 380° C.
[b](Mo/Fe molar ratio)

Example 2

Powder samples of iron—molybdate (synthesized), molybdenum trioxide (synthesized) and ferric oxide (commercially available) were used to catalyze the conversion of a 50–55 sccm stream of methanol/oxygen/helium in the molar ratio of 6/13/81 at a temperature of 300° C. The results showed that a mixture of iron—molybdate catalyst ($MoO_3/Fe_2(MoO_4)_3$) had a higher conversion than ferric oxide, which had a higher conversion than molybdenum trioxide which exhibited a higher conversion than iron—molybdate.

$$MoO_3/Fe_2(MoO_4)_3 >> Fe_2O_3 > MoO_3 > Fe_2(MoO_4)_3$$

Example 3

Figure 1:
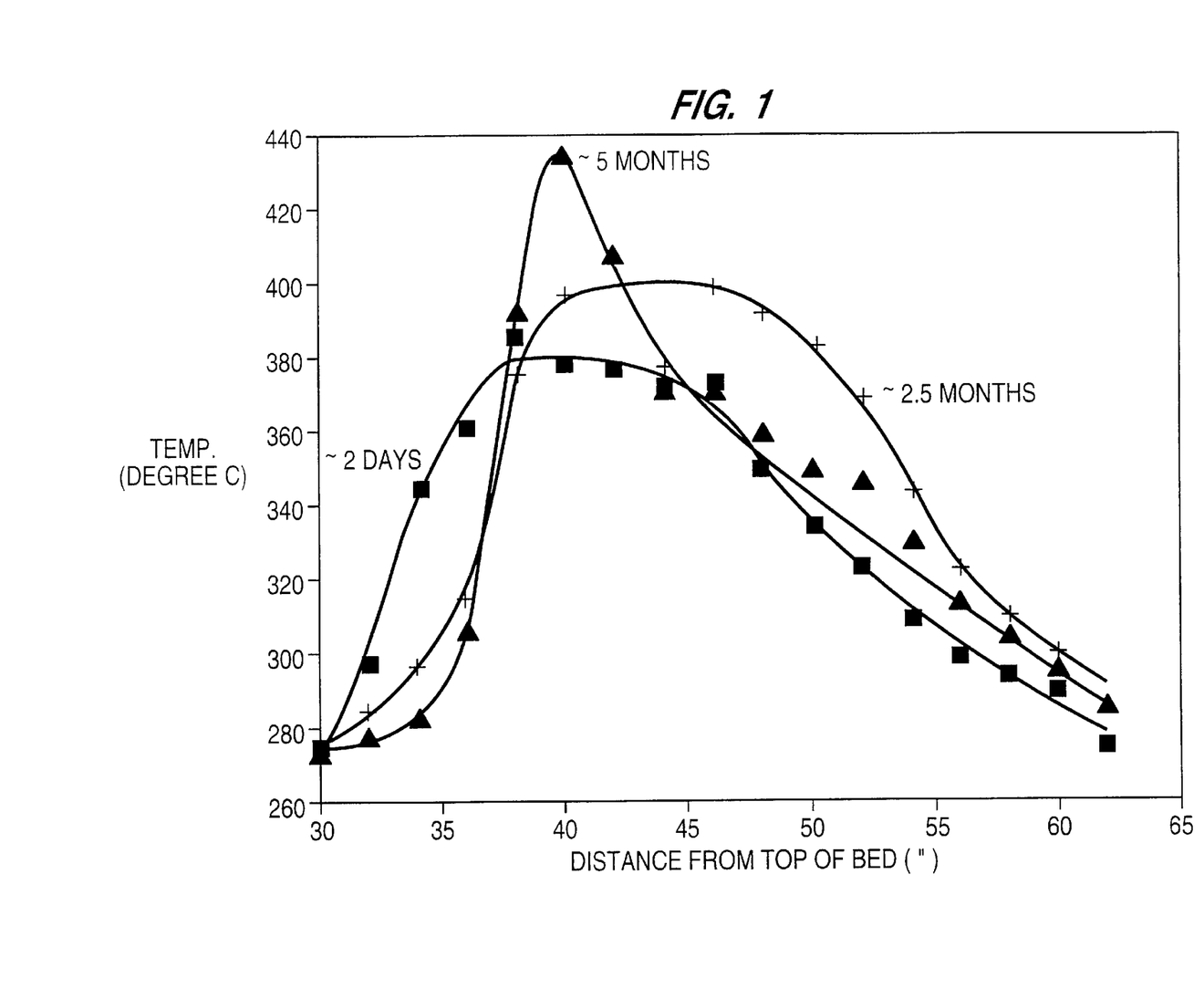
FIG. 1 shows a series of temperature profiles at certain distances in the direction of flow through a catalyst bed at 2 days, 2.5 months, and 5 months of operation.

During a typical methanol conversion process using commercially prepared iron—molybdate catalyst in a cylindrical shape with methanol flowing downwardly through a 65 inch fixed bed of catalyst, the catalyst temperatures at several location were taken at 2 days (fresh system), 2.5 months (mid-life) and at five months (spent). FIG. 1 is a graph of that temperature profile history.

Immediately apparent from the changes in the temperature profile is the development of a "hot spot" in the reactor at a height of about 40 inches from the top of the reactor bed.

Samples of the spent catalyst were removed at three different locations and sectioned for analysis. Location 1 was 33.5 to 35 inches from the top of the reactor (i.e., approximately eleven (11) cylindrical rings weighing about 1.3–1.6 grams total). Location 2 was 42 to 43 inches from the top of the reactor (i.e., approximately eleven (11) cylindrical rings weighing about 1.3–1.6 grams total). Location 3 was 55.5 to 62 inches from the top of the reactor (i.e., one (1) cylindrical ring weighing about 0.074 grams). FIG. 1 shows the temperature profile of the catalyst in the reactor during its operation at various points during the life cycle of the catalyst.

Raman analysis was performed on horizontal cross sections of the fresh and various spent catalysts. The Raman spectra are shown on FIGS. 4 (new catalyst), 5 (top of bed at 5 mos.), 6 (hot spot) and 7 (bottom of bed). The four spectra on each Figure correspond to the interior of the catalyst body (1, 2), the exposed inner (3) surface, and the exposed outer (4,4') surface.

Figure 4:
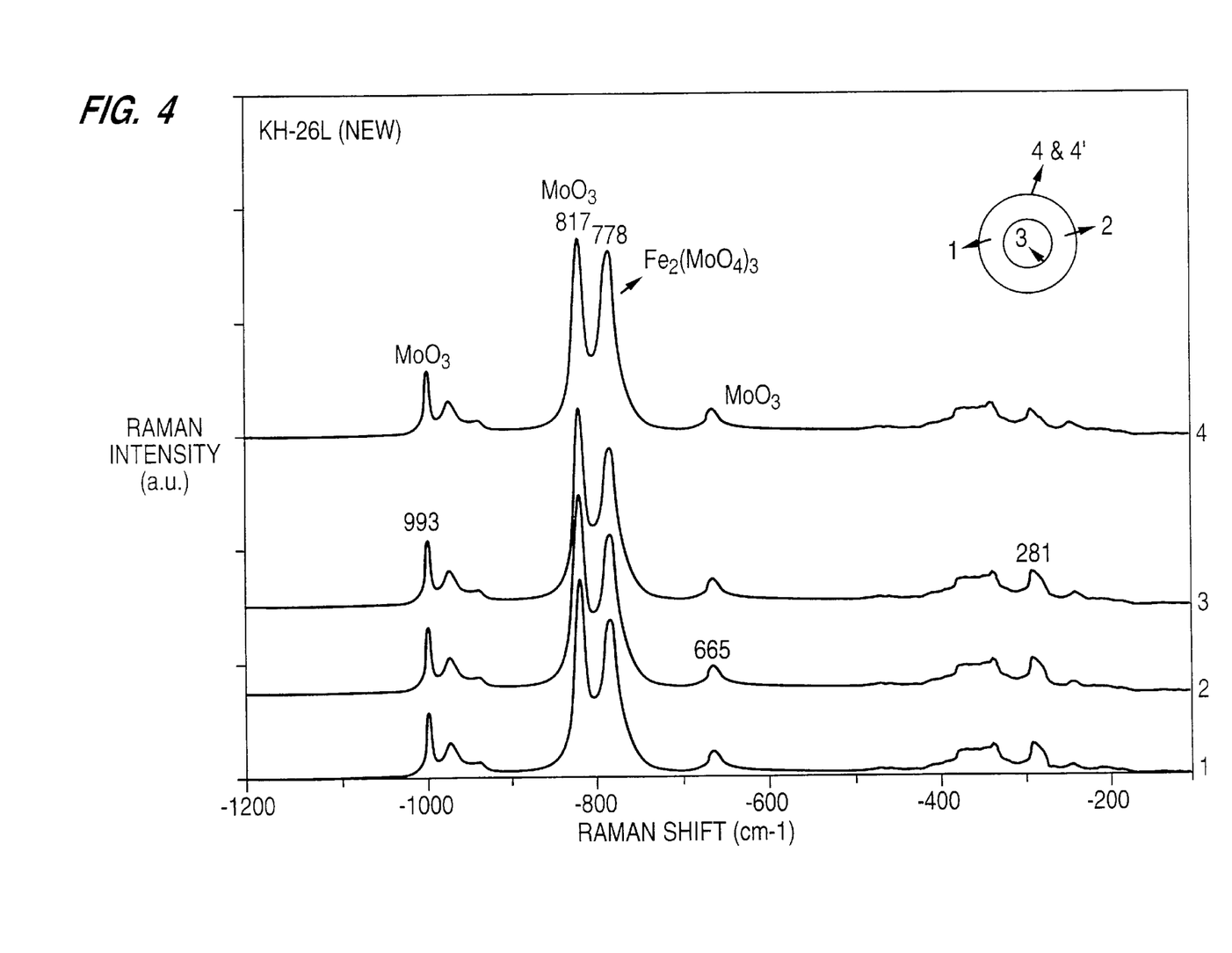
FIGS. 4–7 are results of Raman analysis for horizontally sectioned catalysts from different regions of the reactor. Comparison of the peak shifts shows that iron—molybdate is generally enhanced in exterior catalyst surfaces at the reactor top and "hot spot" regions while the catalyst surfaces at the cooler bottom of the bed are relatively enriched in molybdenum trioxide.
Figure 5:
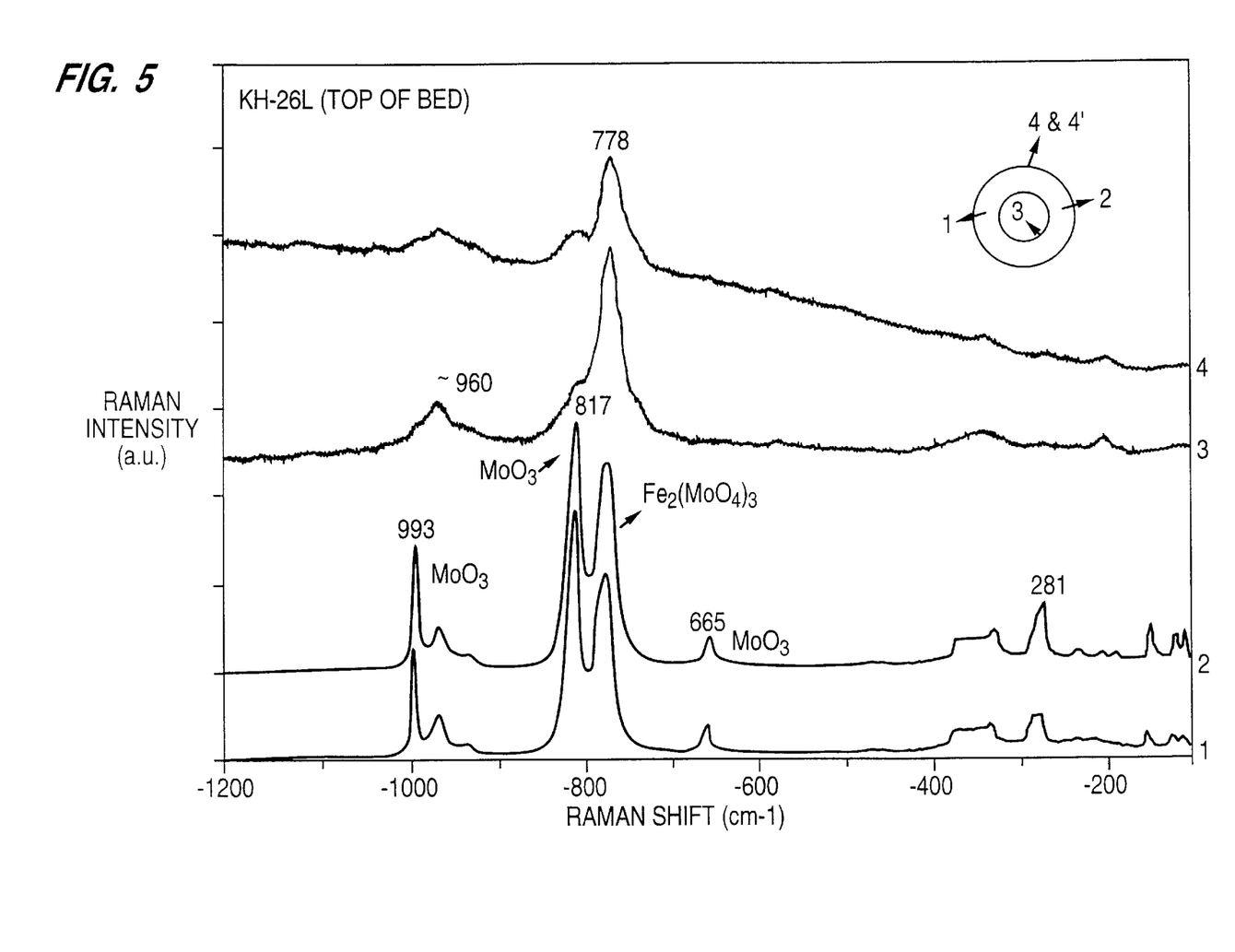
Figure 6:
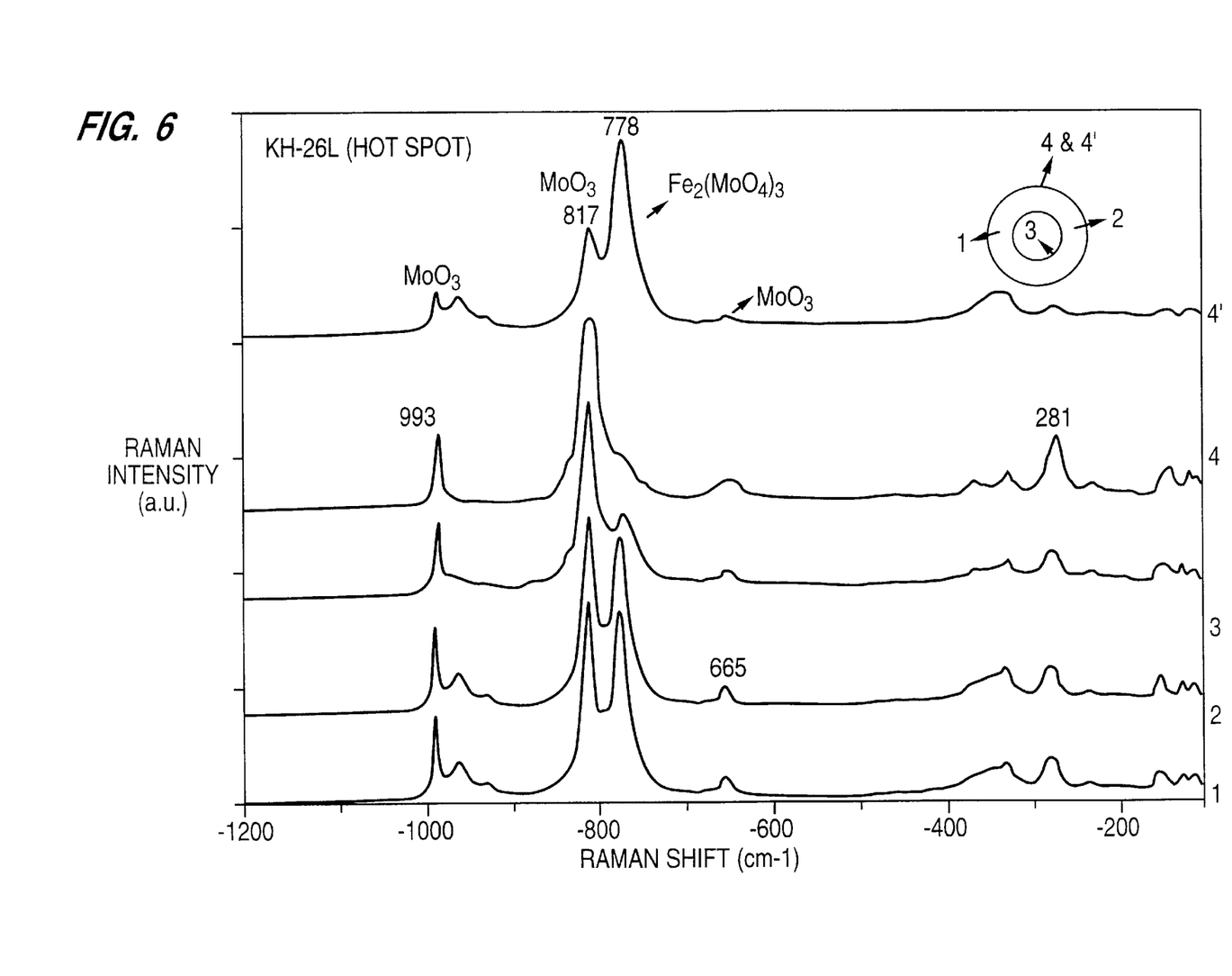
Figure 7:
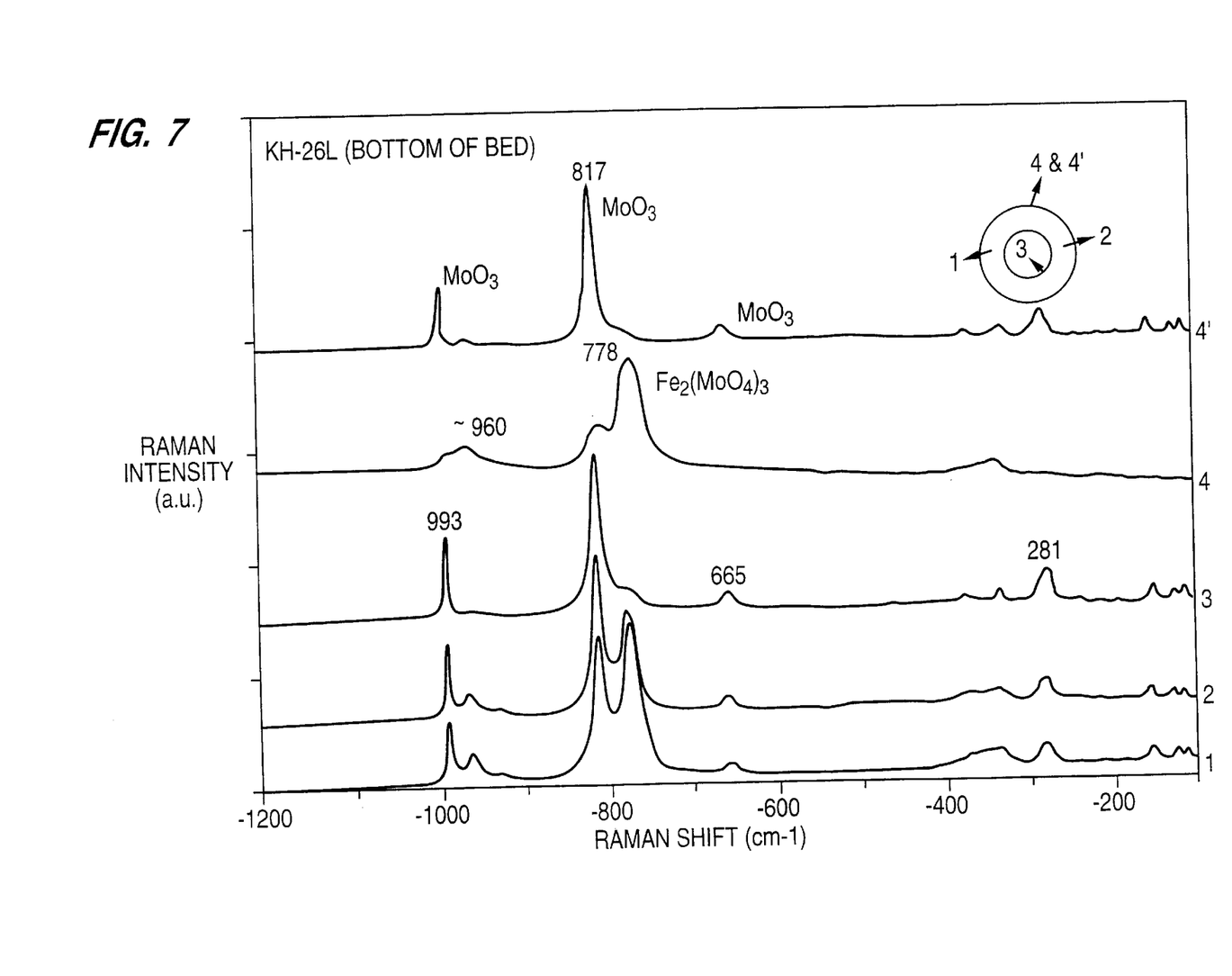

As seen in FIG. 4, the fresh catalyst is made of $MoO_3$ and $Fe_2(MoO_4)_3$ phases that are uniformly distributed throughout the catalyst. Each scan shows a set of peaks that are in the same place and roughly the same relative heights. This is not the same set of peak profiles seen by catalysts either at the top of the spent bed (FIG. 5) or at the bottom of the spent bed (FIG. 7). Catalyst at the top of the bed shows a significant reduction in the relative amount of molybdenum trioxide. The catalyst at the bottom shows the reverse: significant excess of molybdenum trioxide. Catalyst at the hot spot (FIG. 6) shows some reduction in relative amount of molybdenum trioxide at 4' but a significant increase at outer location 4 and inner surface 3.

Examples 4 and 5

Spent catalyst from the top (i.e., 33.5–35 inches) of the catalyst bed was regenerated for 0 (control), 15, 30, 60, and 180 minutes in an oxygen-free, flowing stream (50–55 sccm) of 6% methanol in helium at 300° C. The regenerated catalyst was then used to catalyze the conversion of a 50–55 sccm stream containing methanol, oxygen, and helium at a molar ratio of 6:13:81 at a temperature of 300° C. The performance of the regenerated catalyst is shown in FIGS. 2 and 3 in terms of formaldehyde (HCHO) selectivity, methanol conversion percent, and selectivity for dimethyl ether (DME).

Figure 2:
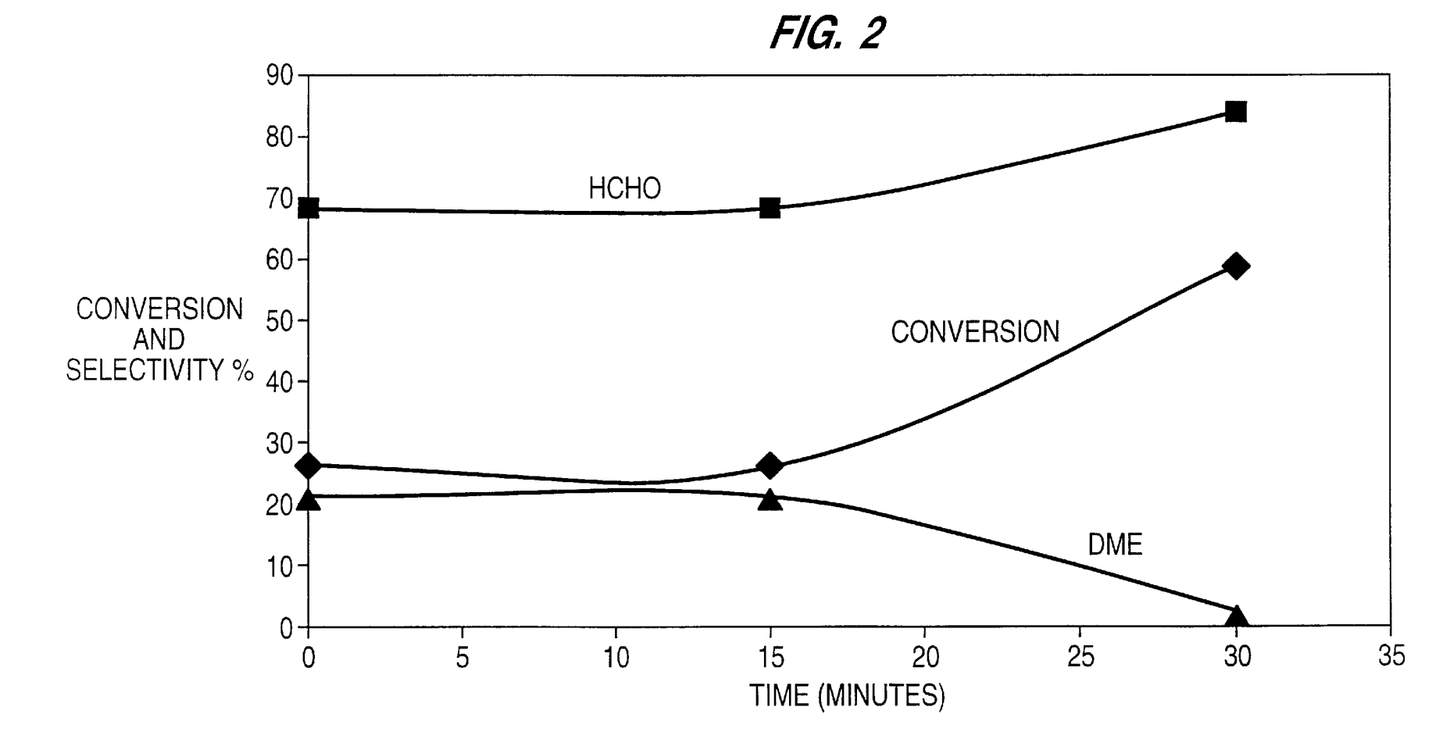
FIG. 2 is a graph showing the increase in conversion and formaldehyde yield and reducing dimethyl ether (DME) production with spent catalyst that has been regenerated for 0, 15, and 30 minutes according to experiment 1.
Figure 3:
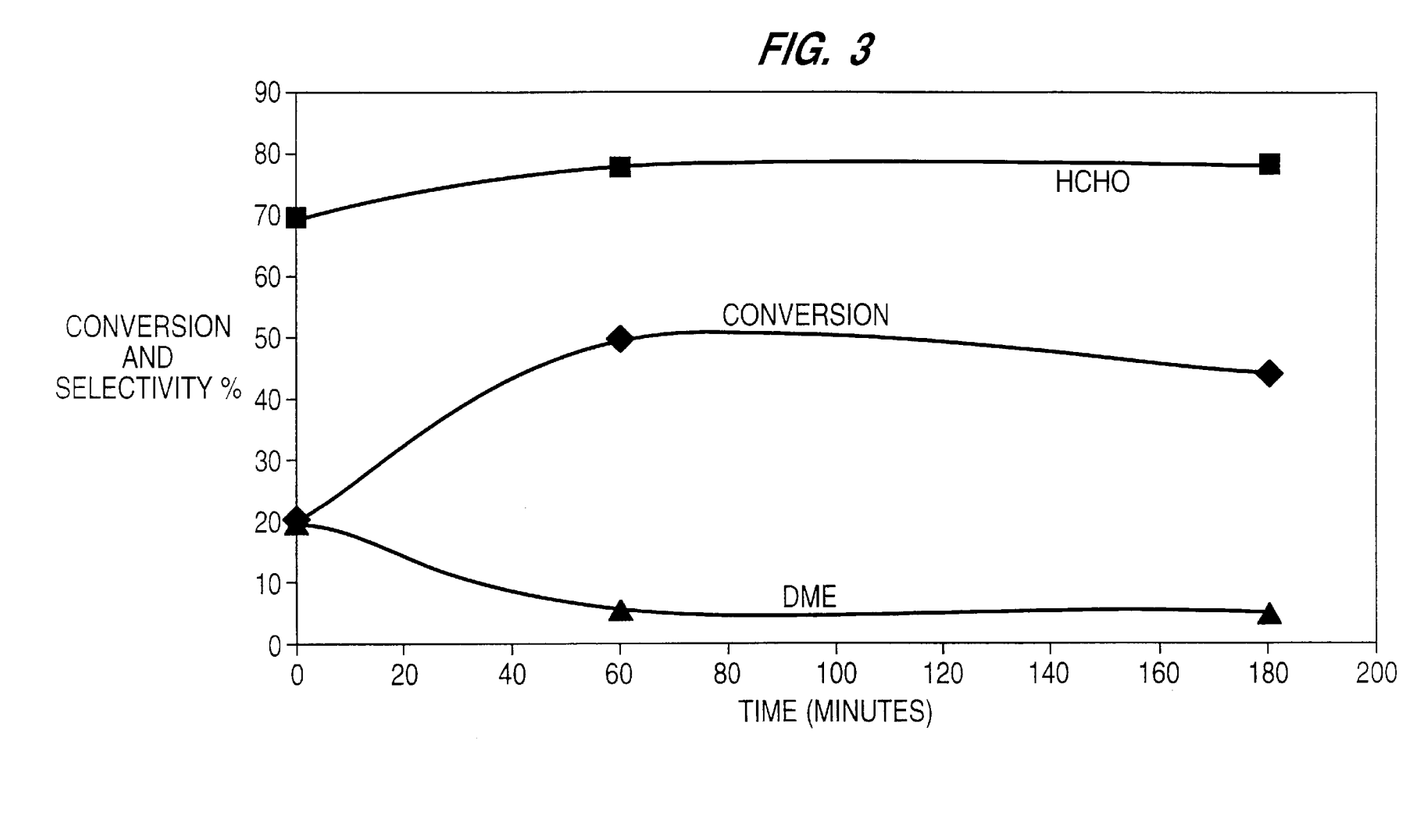
FIG. 3 is a graph of formaldehyde yield, conversion, and DME production in catalyst regenerated for 30, 60, and 180 mins.

As shown in FIG. 2, the spent catalyst initially converted 26.4% of methanol to formaldehyde (67.9%) and dimethyl ether (21.5%). Other substances (methyl formate, dimethoxy methane), not shown in the graphs for simplicity, were also produced. No modifications of conversion or selectivity were observed after regeneration for 15 minutes. When regenerated for 30 minutes, an increase of about two (2) times with respect to the initial conversion was observed. Moreover, the selectivity to formaldehyde reached 84%. The observation that dimethyl ether dropped from 21.5% to 2.4% demonstrates that the weak acid sites were successfully coupled with molybdenum during the regeneration treatment.

The spent catalyst samples of example 5 that were regenerated for 0 (control), 60 and 180 mins presented a similar initial catalytic activity (conversion 19.4%) and selectivity (68.7% to HCHO and 19.4% to DME) to the spent catalyst control of example 4. As shown in FIG. 3, regeneration for 60 minutes increased the conversion of methanol with improved formaldehyde selectivity while the selectivity to dimethyl ether decreased. The trends in increased conversion (about two (2) times) and selectivity (78%) are similar to those obtained when the sample was treated for 30 minutes in accordance with the regeneration treatment of the present invention (ex. 4). No subsequent changes were detected after three hours of treatment with the methanol/helium stream.

Thus, spent iron—molybdate catalysts for formaldehyde production can be effectively and efficiently regenerated by treating the spent catalyst with a methanol/helium gas stream in the absence of oxygen. While helium was used in the preferred embodiment of the present invention, it is contemplated that any suitable inert gas can be used in the present invention.

As shown by comparing FIGS. 2 and 3, formaldehyde (HCHO) selectivity % increases with in situ regeneration provided that this in situ regeneration treatment is performed for at least about thirty (30) minutes. Further regeneration does not increase conversion % or formaldehyde (HCHO) selectivity % when the time is increased to one(1) hour or three (3) hours for the spent catalyst employed. It is believed that there may be some variations in the time for regeneration to the point of diminishing returns that one with no more than an ordinary level of skill in this art will be able to determine with no more than routine screening tests. Table 2 summarizes the test results.

TABLE 2

| Sample | Conversion % (300° C.) | Selectivity % | | | | |
|---|---|---|---|---|---|---|
| | | HCHO | DME | DMM | MF | Other |
| $Fe_2(MoO_4)_3$ | 1.0 | 56.1 | 43.8 | — | — | — |
| $MoO_3$ | 1.7 | 84.1 | 12.0 | 3.9 | — | — |
| $Fe_2O_3$ | 2.6 | 43.7 | 50.2 | 5.2 | — | — |
| $Fe_2(MoO_4)_3/MoO_3$ | 7.4 | 85.3 | 11.7 | 3.0 | — | — |
| spent catalyst location[1] | | | | | | |
| 33½–35 | 26.4 | 67.9 | 21.5 | 1.7 | 1.5 | 7.3 |
| 42–43 | 38.2 | 82.3 | 4.5 | 3.1 | 0.8 | 9.3 |
| 55½–62 | 53.5 | 87.3 | 2.8 | 0.7 | 0.6 | 8.6 |
| after regeneration treatment[2] | | | | | | |
| 33½–35 | 58.8 | 84.0 | 2.4 | 1.0 | 0.95 | 11.5 |
| 42–43 | 59.2 | 84.1 | 2.5 | 1.0 | 1.3 | 11.1 |
| 55½–62 | 51.9 | 86.5 | 2.9 | 0.8 | — | 9.7 |

HCHO: formaldehyde; DME: dimethyl ether; DMM: dimethoxy methane and MF: methyl formate.
[1]in inches from top of 65 inch reactor bed prior to regeneration treatment
[2]of spent catalyst It should be noted that catalyst at the bottom of the fixed bed already exhibits an excess of molybdenum trioxide.

While various alterations and permutations of the invention are possible, the invention is to be limited only by the following claims and equivalents.

We claim:

1. A method for in situ regeneration of spent iron—molybdate catalyst that has been used for methanol conversion to formaldehyde, said method comprising the steps:

exposing said spent iron—molybdate catalyst to an oxygen-free gas stream comprising methanol and an inert gas at elevated temperature for a sufficient time to regenerate the iron—molybdate catalyst.

2. The method of claim 1 wherein the inert gas is helium.

3. The method of claim 1 wherein the gas stream of methanol and inert gas is contacted with the iron—molybdate catalyst for at least thirty minutes.

4. The method of claim 1 wherein said temperature is within the range from about 250–350° C.

5. The method of claim 1 wherein said temperature is at about the same temperature as the catalyst temperature used during said conversion of methanol to formaldehyde.

6. The method of claim 1 wherein said catalyst comprises coprecipitated molybdate and ferric oxide.

7. The method of claim 6 wherein said catalyst has been made by coprecipitating an ammonium molybdate with iron nitrate solution.

* * * * *